(12) United States Patent
Yeaman et al.

(10) Patent No.: US 6,743,769 B1
(45) Date of Patent: Jun. 1, 2004

(54) ANTIMICROBIAL PEPTIDES AND DERIVED METAPEPTIDES

(75) Inventors: Michael R. Yeaman, Torrance, CA (US); Alexander J. Shen, Torrance, CA (US)

(73) Assignee: Harbor-UCLA Research and Education Institute, Torrance, CA (US)

( * ) Notice: Subject to any disclaimer, the term of this patent is extended or adjusted under 35 U.S.C. 154(b) by 0 days.

(21) Appl. No.: 09/525,269

(22) Filed: Mar. 13, 2000

Related U.S. Application Data

(62) Division of application No. 09/025,319, filed on Feb. 18, 1998, now abandoned.

(51) Int. Cl.[7] .............................. A61K 38/04; C07K 7/00

(52) U.S. Cl. .............................. 514/2; 514/13; 514/14; 514/17; 530/300; 530/326; 530/327; 530/330

(58) Field of Search ................................. 530/300, 330, 530/326, 327; 514/2, 13, 14, 17

(56) References Cited

U.S. PATENT DOCUMENTS

| | | |
|---|---|---|
| 5,409,898 A | 4/1995 | Darveau et al. |
| 5,834,430 A | 11/1998 | Porro et al. |

FOREIGN PATENT DOCUMENTS

| | | |
|---|---|---|
| WO | WO 99/42119 | 8/1999 |
| WO | WO 00/18922 | 4/2000 |
| WO | WO 00/22170 | 4/2000 |
| WO | WO 00/31263 | 6/2000 |

OTHER PUBLICATIONS

Michael R. Yeaman; Platelet Microbicidal Proteins (PMPs) Differentially Depolarize and Permeabilize the Staphylococcus aureus Cytoplasmic Membrane to Effect Microbicidal Activity In Vitro; 97th ASM General Meeting; Miami Beach, FL; May 4–8, 1997; 1 page.

Y.O. Tang, et al.; "Microbicidal and Synergistic Activities of Human Platelet Factor–4 (Hpf–4) and Connective Tissue Activating Peptide–3 (CTAP–3)"; 1995 ASH 37th Annual Meeting, Seattle, Washington; Dec. 1–5, 1995; 1 page.

Richard P. Darveau, et al.; Peptides Related to the Carboxyl Teminus of Human Platelet Factor IV with Antibacterial Activity; The American Society for Clinical Investigation, Inc.; vol. 90, Aug. 1992, pp. 447–455.

Michael R. Yeaman, et al.; Parial Characterization and Staphylocidal Activity of Thrombin–Induced Platelet Microbicidal Protein; Infection and Immunity, Mar. 1992, pp. 1202–1209.

Y.O Tang, et al., "Purification, Characterization, and Antimicrobial Properties of Peptides Released From Thrombin–Induced Human Platelets"; 1995 ASH 37th Annual Meeting, Seattle, WA; Dec. 1–5, 1995; 1 page.

Michael R. Yeaman, et al.; Thombin–Induced Rabbit Platelet Microbicidal Protein Is Fungicidal In Vitro; Antimicrobial Agents and Chemotherapy, Mar. 1993, pp. 546–553.

Naveen Pathak, et al., "Comparison of the Effects of Hydrophobicity, Amphiphilicity and α–Helicity on the Activities of Antimicrobial Peptides; Proteins: Structure, Function, and Genetics 22:182–186" (1995).

Klenk et al., Chemical Abstract No. 128:84966; "The Complete Genome Sequence of the Hyperthomophilic, Sulfate–Reducing Archaeon Archaeoglobus Fulgidus"; Nature (London) 1997, vol. 390(6658) Nov. 1997, pp. 364–370.

Mee et al., Chemical Abstract No. 126:293592; "Design of Active Analogs of a 15–residue Peptide Using D–optimal Design, QSAR and a Combinatorial Search Algorithm"; J. Pept. Res. 1997, vol. 49(1), pp. 89–102.

Margaret O. Dayhoff, "Atlas of Protein Sequence and Structure," 1972, vol. 5, National Biomedical Research Foundation, Washington, D.C.,pp. 89–99.

Science vol. 256, "Biology Approaches the Teraflop Era," Apr. 24, 1992, pp. 440–442.

Bayer et al., "In Vitro Resistance of Staphylococcus aureus to Thrombin–Induced Platelet Microbicidal Protein is Associated with Alterations in Cytoplasmic Membrane Fluidity," Infection and Immunity 68(6):3548–3553, Jun. 2000.

Bayer et al., "Hyperproduction of Alpha–Toxin by Staphylococcus aureus Results in Paradoxically Reduced Virulence in Experimental Endocarditis: a Host Defense Role for Platelet Microbicidal Proteins," Infection and Immunity 65(11): 4652–4660, Nov. 1997.

Bayer et al., "In Vitro Resistance to Thrombin–Induced Platelet Microbicidal Protein among Clinical Bacteremic Isolates of Staphylococcus aureus Correlates with and Endovascular Infectious Source," Antimicrobial Agents and Chemotherapy 42(12): 3169–3172, Dec. 1998.

Dhawan et al., "Influence of In Vitro Susceptibility Phenotype against Thrombin–Induced Platelet Microbicidal Protein on Treatment and Prophylaxis Outcomes of Experimental Staphylococcus aureus Endocarditis," Journal of Infectious Diseases 180:1561–1568, 1999.

(List continued on next page.)

Primary Examiner—Bennett Celsa
(74) Attorney, Agent, or Firm—McDermott, Will & Emery

(57) ABSTRACT

The peptides and derivative metapeptides based upon natural antimicrobial peptides have potent and broad spectrum activity against pathogens exhibiting multiple antibiotic resistance. In addition, they exhibit lower inherent mammalian cell toxicities than conventional antimicrobial peptides, and overcome problems of toxicity, immunogenicity, and shortness of duration of effectiveness due to biodegradation, retaining activity in plasma and serum. The peptides and derivative metapeptides exhibit rapid microbicidal activities in vitro, can be used to potentiate conventional antimicrobial agents, to potentiate other antimicrobial peptides, and are active against many organisms that exhibit resistance to multiple antibiotics currently in existence.

1 Claim, 3 Drawing Sheets

OTHER PUBLICATIONS

Dhawan et al., "In Vitro Resistance to Thrombin–Induced Platelet Microbicidal Protein Is Associated with Enhanced Progression and Hematogenous Dissemination in Experimental *Staphylococcus aureus* Infective Endocarditis," *Infection and Immunity* 66(7) 3476–3479, Jul. 1998.

Dhawan et al., "Phenotypic Resistance to Thrombin–Induce Platelet Microbicidal Protein In Vitro Is Correlated with Enhanced Virulence in Experimental Endocarditis Due to *Staphylococcus aureus*," *Infection and Immunity* 65(8):3293–3299, Aug. 1997.

Koo et al., "Staphylocidal Action of Thrombin–Induced Platelet Microbicidal Protein is Not Solely Dependent on Transmembrane Potential," *Infection and Immunity* 64(3): 1070–1074, Mar. 1996.

Koo et al., "The Cytoplasmic Membrane Is a Primary Target for the Staphylocidal Action of Thrombin–Induced Platelet Microbicidal Protein," *Infection and Immunity* 65(11): 4795–4800, Nov. 1997.

Koo et al., "Membrane Permeabilization by Thrombin–Induced Platelet Microbicidal Protein 1 Is Modulated by Transmembrane Voltage Polarity and Magnitude," *Infection and Immunity* 67(5): 2475–2481, May 1999.

Kupferwasser et al., "Plasmid–Mediated Resistance to Thrombin–Induced Platelet Microbicidal Protein in Staphylococci: Role of the qacA Locus," *Antimicrobial Agents and Chemotherapy* 43(10): 2395–2399, Oct. 1999.

Stover, C.K. et al., "Complete genome sequence of *Pseudomonas aeruginosa* PA01, an opportunistic pathogen," *Nature* 406:959–964, Aug. 31, 2000.

Wu et al., "In Vitro Resistance to Platelet Microbicidal Protein Correlates with Endocarditis Source Among Bacteremic Staphylococcal and Streptococcal Isolates," *Antimicrobial Agents and Chemotherapy* 38(4): 729–732, Apr. 1994.

Xiong et al., "In Vitro Antibacterial Activities of Platelet Microbicidal Protein and Neutrophil Defensin against *Staphylococcus aureus* Are Influenced by Antibiotics Differing in Mechanism of Action," *Antimicrobial Agents and Chemotherapy* 43(5): 1111–1117, May 1999.

Yeaman et al., "*Staphylococcus aureus* Susceptibility to Thrombin–Induced Platelet Microbicidal Protein is Independent of Platelet Adherence and Aggregation In Vitro," *Infection and Immunity* 60(4): 2368–2374, Jun. 1992.

Yeaman et al., "Platelet Microbicidal Protein Enhances Antibiotic–Induced Killing of and Postantibiotic Effect in *Staphylococcus aureus*," *Antimicrobial Agents and Chemotherapy* 36(8): 1665–1670, Aug. 1992.

Yeaman et al., "Thrombin–Induced Rabbit Platelet Microbicidal Protein is Fungicidal In Vitro," *Antimicrobial Agents and Chemotherapy* 37(3): 546–553, Mar. 1993.

Yeaman et al., "Resistance to Platelet Microbicidal Protein Results in Increased Severity of Experimental *Candida albicans* Endocarditis," *Infection and Immunity* 64(4): 1379–1384, Apr. 1996.

Yeaman et al., "Platelet Microbicidal Proteins and Neutrophil Defensin Disrupt the *Staphylococcus aureus* Cytoplasmic Membrane by Distinct Mechanisms of Action," *The Journal of Clinical Investigation* 101(1): 178–187, Jan. 1998.

Yeaman et al., "Fluconazole and Platelet Microbicidal Protein Inhibit Candida Adherence to Platelets In Vitro," *Antimicrobial Agents and Chemotherapy* 38(7): 1460–1465, Jul. 1994.

Yeaman et al., "Platelet Microbicidal Protein Alone and in Combination with Antibiotics Reduces *Staphylococcus aureus* Adherence to Platelets In Vitro," *Infection and Immunity* 62(8): 3416–3423, Aug. 1994.

Yeaman et al., "Purification and In Vitro Activities of Rabbit Platelet Microbicidal Proteins," *Infection and Immunity* 65(3): 1023–1031, Mar. 1997.

Yeaman, M., "The Role of Platelets in Antimicrobial Host Defense," *Clinical Infectious Diseases* 25:951–968, 1997.

Yeaman et al., "Structural Correlates in Mechanisms of Cationic Antimicrobial Peptide Action," *Presented at the 38th ICAAC, San Diego, California, Sep. 24–27, 1998*.

ANTIMICROBIAL PEPTIDES AND DERIVED METAPEPTIDES

RELATED APPLICATIONS

This is a divisional of Ser. No. 09/025,319, filed Feb. 18, 1998 now abandoned.

BACKGROUND OF THE INVENTION

1. Field of the Invention

This invention relates generally to antimicrobial agents, and more specifically pertains to peptides useful as antimicrobial agents for the prevention and treatment of infections caused by organisms, such as bacteria and fungi, many of which are resistant to conventional antibiotics.

2. Description of Related Art

Human infections due to antibiotic-resistant bacteria and fungi are increasing in frequency and severity. Microbial pathogens exhibiting resistance to one or more antibiotics can now commonly be found in community and nosocomial settings. Antibiotic resistant pathogens currently of the greatest concern are methicillin (multiple) resistant *Staphylococcus aureus* (MRSA), vancomycin resistant *Enterococcus faecalis* and *Enterococcus faecium* (VRE), beta lactam resistant *Streptococcus pneumoniae* (MDRSPn) or *Streptococcus pyogenes* (BRSPy), aminoglycoside resistant *Pseudomonas aeruginosa* (ARPA), and azole resistant *Candida albicans* (ARCA).

Antimicrobial peptides have heretofore generally been considered to have undesirable toxicity, immunogenicity, and short half-lives due to biodegradation. However, endogenous antimicrobial peptides are believed to be integral to non-oxidative mechanisms of antimicrobial host defense. Stable, peptide-resistant mutants are rare, likely because microbicidal peptides appear to target the cytoplasmic membrane or other essential structures of pathogens. Investigations conducted over the past decade have demonstrated the existence of potent microbicidal peptides from various mammalian tissues. Perhaps the most thoroughly studied among these are defensins from neutrophil azurophilic granules. Related peptides such as β-defensins and cryptdins have also been isolated and characterized. To date, nearly 20 distinct defensins have been found in mammalian neutrophils.

Aside from neutrophils, the probability that platelets play an integral role in host defense against infection has been demonstrated by the following observations: i) platelets are the earliest and predominant cells at sites of microbial infection of vascular endothelium; ii) platelets adhere to and internalize microbial pathogens; iii) bacterial, fungal, and protozoal pathogens are damaged or killed by activated platelets in vitro; iv) thrombocytopenia increases susceptibility to and severity of some infections; v) rabbit and human platelets release platelet microbicidal proteins (PMPs) when stimulated with microorganisms or platelet agonists integral to infection in vitro; and vi) PMPs exert rapid and potent microbicidal activities against a broad spectrum of pathogens in vitro. It has been hypothesized that PMPs substantially contribute to platelet antimicrobial host defense by direct microbicidal actions, and may amplify cell mediated immune mechanisms such as neutrophil microbicidal activity. Similar to defensins, PMPs appear to disrupt microbial cytoplasmic membranes to achieve microbicidal activity. Present data indicates that PMP-2, tPMP-1, and defensin hNP-1 employ distinct mechanisms, and that these differences are related to differences in protein structure.

The majority of known mammalian antimicrobial peptides have been localized within leukocytes (e.g., defensins), or secreted onto epithelial surfaces such as intestinal lumen or tracheal epithelium (e.g., cryptdins, tracheal antimicrobial peptide). Prohibitive levels of mammalian cell toxicity have been noted with many of these peptides when they have been tested as antimicrobial therapeutics. In contrast, PMPs exert potent in vitro microbicidal activity against a broad spectrum of bacteria and fungi under physiological conditions that exist in the intravascular space. Several PMPs are released from platelets stimulated with agonists associated with infection. Therefore, in response to tissue injury, PMPs are likely released into the mammalian bloodstream at localized sites of infection. In preliminary studies, tPMP-1 and PMP-2 have been found to cause minimal damage of human erythrocytes or vascular endothelial cells in vitro as compared with defensin hNP-1. PMPs and defensins exert potent microbicidal activity against bacterial and fungal pathogens, which has been observed at concentrations as low as 0.5 μg/ml in vitro, comparable to potent conventional antimicrobial agents such as aminoglycosides or amphotericin B.

A large family of antimicrobial peptides from mammalian platelets has also been isolated, and amino acid compositions and primary structures of endogenous antimicrobial peptides originating from mammalian and non-mammalian tissues now constitute a database of over 300 antimicrobial peptides. Recent advances in peptide structural analyses have provided important new information regarding the relationship between structure and microbicidal activities among these peptides. For example, the fact that many antimicrobial peptides are small, cationic, and contain amphiphilic α-helical domains is well established.

It would be desirable to provide peptides that are active against organisms that exhibit resistance to antibiotics, for use either independently or in combination to potentiate conventional antimicrobial agents or other antimicrobial peptides. It is also desirable to provide microbicidal peptides that are based upon natural antimicrobial peptides, to overcome problems of toxicity and immunogenicity. To overcome short half-life due to degradation, such peptides should be resistant to proteolytic degradation, and should be stable in temperatures as high as 80° C., and in extremes of alkalinity and acidity, ranging from about pH 2 to about pH 10, for example. It is further desirable that such peptides should be amenable to chemical synthesis or recombinant DNA-based expression, facilitating their production in quantities necessary for testing. The present invention addresses, at least in part, these and other needs.

SUMMARY OF THE INVENTION

Briefly, and in general terms, the present invention provides for peptides and derivative metapeptides that likely target the microbial cytoplasmic lead to ensuing effects on intracellular targets. This, along with secondary effects on intracellular functions such as macromolecular synthesis or bioenergetics, leads to overall cellular disruption and eventually to death of the targeted microbes.

The invention accordingly provides for an antimicrobial peptide for potentiating antimicrobial agents active against pathogenic organisms such as bacteria and fungi. In one presently preferred embodiment, the antimicrobial peptide comprises a peptide having an amino acid sequence selected from the group of amino acid sequences consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX, where B is at least one positively charged amino acid, X is at least one non-polar, hydrophobic amino acid, and Z is at least one aromatic amino acid. In a presently preferred aspect of the invention, B is selected from the group of amino acids consisting of lysine, arginine, histidine, and combinations thereof; X is selected from the group of amino acids consisting of leucine, isoleucine, alanine, valine, and combinations thereof; and Z is selected from the group of amino acids consisting of phenylalanine, tryptophan, tyrosine and combinations thereof. In another aspect, the peptide or derived metapeptide of the invention can further comprise D-isomeric amino acids. In another aspect, the peptide or derived metapeptide of the invention can further comprise a retromeric sequence of amino acids. In a further aspect, the peptide or derived metapeptide of the invention can further comprise a modified amino acid group selected from the group consisting of N-$^\epsilon$monomethyl-lysine, fluorinated amino acids, and combinations thereof in direct or retromeric sequences.

The peptides and derivative metapeptides of the invention exert potent, broad spectrum antimicrobial activities in vitro, exhibit rapid microbicidal activities in vitro, can be used to potentiate conventional antimicrobial agents, to potentiate other antimicrobial peptides, and are active against many organisms that exhibit resistance to multiple antibiotics. The peptides and derivative metapeptides of the invention can be designed to overcome problems of toxicity, immunogenicity, and shortness of duration of effectiveness due to biodegradation, retaining activity in plasma and serum, since they are based upon natural antimicrobial peptides that have lower inherent mammalian cell toxicities than conventional antimicrobial peptides. The peptides and derivative metapeptides of the invention also are linear, and have a low molecular mass, reducing the likelihood of producing immunogenic effects, since small peptides have a reduced likelihood of being immunogenic as compared with larger parent proteins. Many peptide designs are inherently resistant to proteolytic degradation, and exhibit stability in temperatures as high as 80° C., and in extremes of alkalinity and acidity, ranging from pH 2 to pH 10, for example. Substitutions of D- or other unusual amino acids into the RP-1, Sequence No. 3, RP-13, Sequence No. 14, and derivative metapeptide design templates may also increase their degradation time significantly, extending their half-life. Furthermore, these peptides are quite amenable to chemical synthesis, facilitating their production in quantities necessary for use and evaluation in vitro.

These and other aspects and advantages of the invention will become apparent from the following detailed description, the accompanying drawings and sequence listing, which illustrate by way of example the features of the invention.

DETAILED DESCRIPTION OF THE PREFERRED EMBODIMENTS

Figure 1:
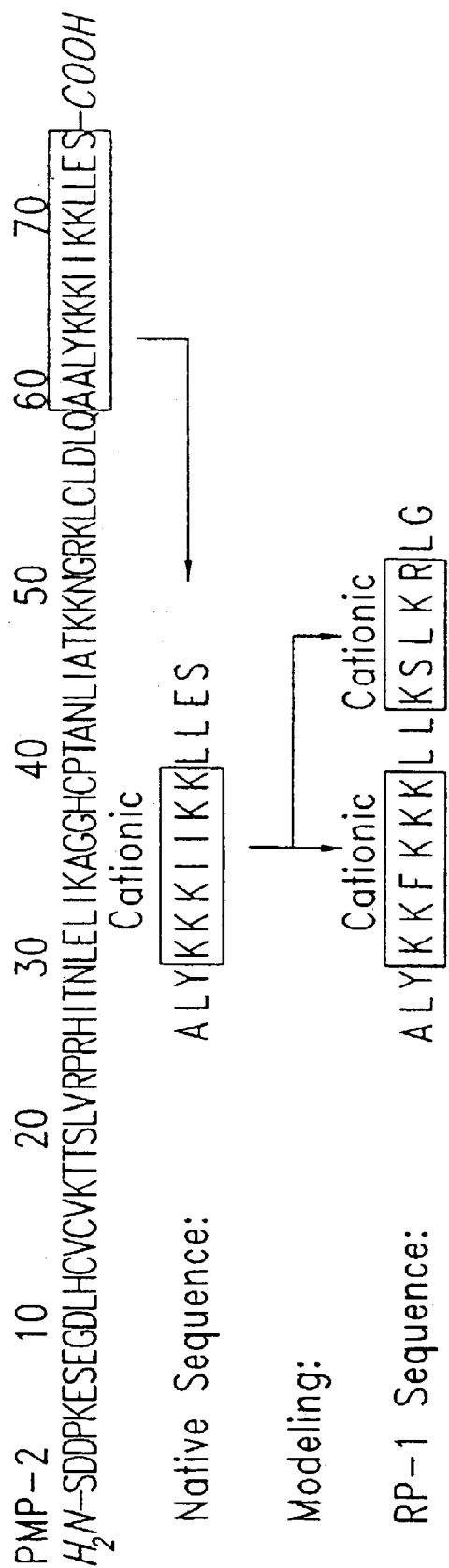
FIG. 1 is a diagram of the design of RP-1, Sequence No. 3, from modeling of a microbicidal domain of PMP-2.

While natural antimicrobial peptides can be useful in combating pathogens exhibiting resistance to multiple antibiotics, either independently or in combination with antibiotic regimens or other antimicrobial peptides, conventional antimicrobial peptides have heretofore been viewed as being undesirably toxic, immunogenic, and short-lived.

As is illustrated in the drawings, the invention is accordingly embodied in novel, improved antimicrobial peptides designed from unique templates to act to inhibit or kill microorganisms that are otherwise resistant to existing antibiotics. The principal peptides, designated RP-1, Sequence No. 3, and RP-13, Sequence No. 14, were designed based in part upon microbicidal domains from platelet microbial proteins 1 and 2 (PMP-1 and PMP-2) as discussed in Yeaman, M. R., et al., "Purification and in vitro activities of rabbit platelet microbicidal proteins," Infect. Immun. 65:1023–1031, 1997. The microbicidal peptides RP-1, Sequence No. 3, and RP-13, Sequence No. 14, can also be used as structural templates from which derived peptides can be modeled and synthesized. These peptides, and derived analogues, may eventually be developed as therapeutic agents to significantly improve treatment of life threatening infections in humans due to organisms resistant to conventional antibiotics.

In addition to parameters known to be associated with antimicrobial activity, specific features have been identified which appear to be integral to maximal peptide microbicidal activity. These include: 1) hydrophobic moment ($M_H$); 2) charge surface area; 3) charge density; and 4) hydrophobic density.

The present invention applies a model which predicts relative antimicrobial activity for a given amino acid sequence. This model takes into account the following equation for determination of the mean hydrophobic moment:

$$M_H = \frac{\left[\sum_{n=1}^{N} H_n \sin(\delta n)^2 + H_n \cos(\delta n)^2\right]^{1/2}}{N}$$

where N is the number of residues, $H_n$ is the hydrophobicity of the nth residue, $\alpha$ is the alpha helicity index (helical fraction), $\beta$ is the beta-sheet index (sheet fraction), $\delta$ is the repeat angle, 100°, and $M_H$ is the mean hydrophobic moment. Use of the variables $\alpha$ and $\beta$ are described below.

Many cationic microbicidal peptides are known to exhibit amphiphilic $\alpha$-helical or $\beta$-sheet conformation. It is also known that many antimicrobial peptides possess domains rich in hydrophobic amino acids. The mean hydrophobic moment $M_H$ dually assesses these parameters; and $M_H$ is essentially the amphiphilicity of a peptide in an $\alpha$-helical conformation. This model integrates mass, charge, hydrophobicity, and predicted secondary structure, to project the likelihood that a peptide will conform to an amphiphilic $\alpha$-helical or $\beta$-sheet structure with features maximizing those believed to be integral to antimicrobial activity. In this model, amphiphilicity is among the most predictive parameters of actual antimicrobial activity. The inventors have recognized that potent microbicidal peptides contain distinct cationic and hydrophobic domains. The above model has been refined to integrate $M_H$ and α-helical or β-sheet conformation in the context of such domains. In this model, peptide microbicidal activity (predicted MIC, also $P_{MIC}$) is inversely related to $M_H$ and α-helicity such that: $P_{MIC}=1/\propto[(M_H)\cdot(\alpha_{peptide})]$. Similarly, β-sheet peptides will be assessed for $P_{MIC}$ as follows: $P_{MIC}=1/\propto[(M_H)\cdot(\beta_{peptide})]$. β is the β sheet index (sheet fraction). In either case, the lower the $P_{MIC}$, the greater the predicted microbicidal activity. This model has proven successful in designing templates RP-1, Sequence No. 3, and RP-13, Sequence No. 14, and derived metapeptides, discussed further below.

Figure 2A:
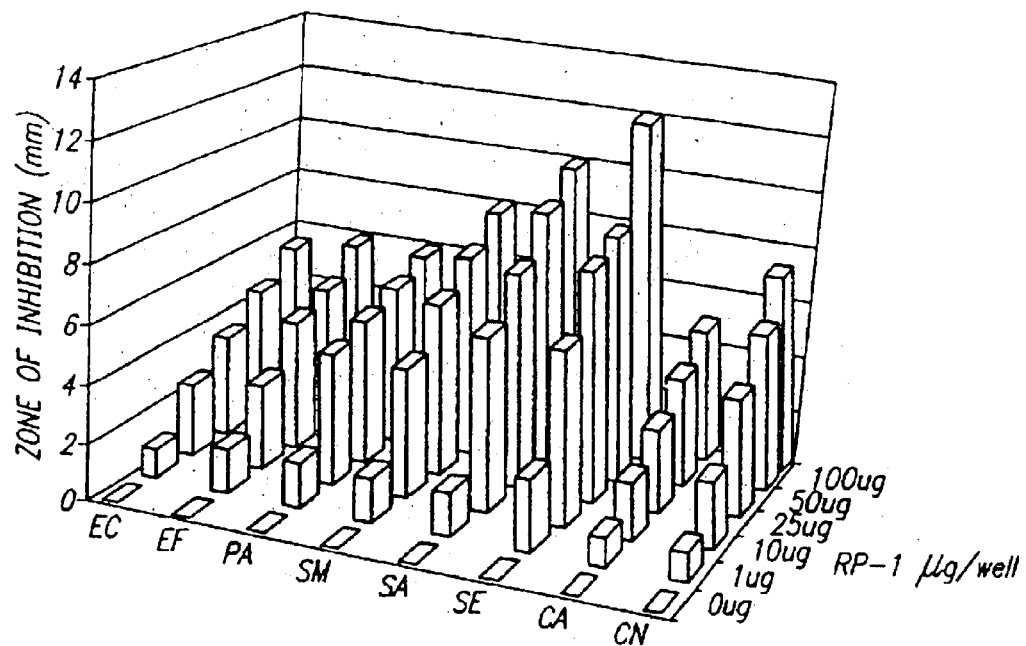
FIG. 2A is a three-dimensional graph of the antimicrobial spectra of RP-1, Sequence No. 3, in vitro (radial diffusion assay)
Figure 2B:
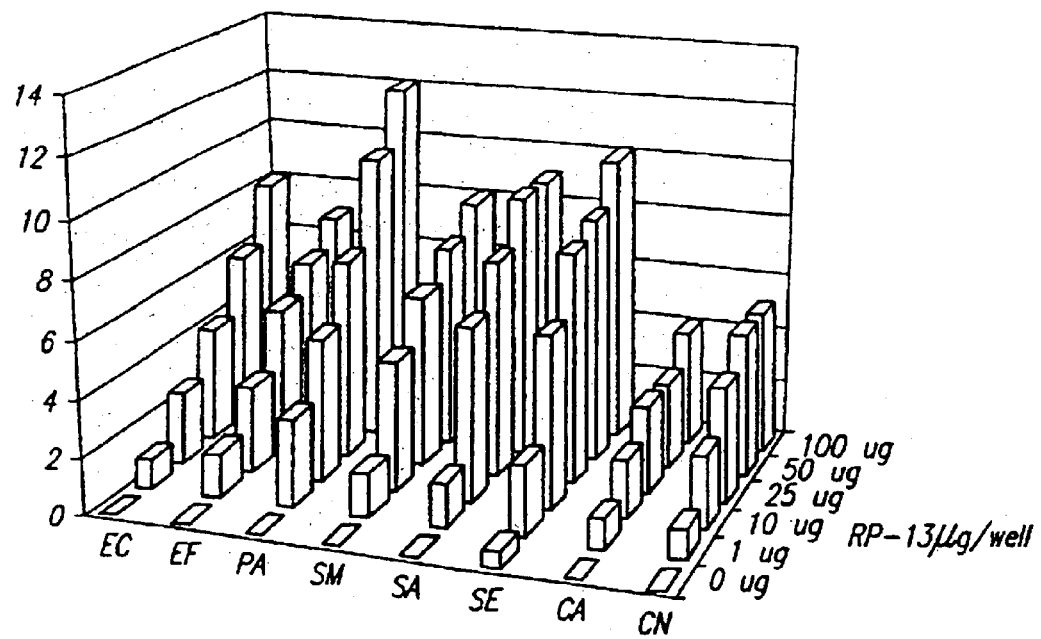
FIG. 2B is a three-dimensional graph of the antimicrobial spectra of RP-13, Sequence No. 14, in vitro (radial diffusion assay)

The peptide model has been used according to the principles of the invention to design RP-1, Sequence No. 3, and RP-13, Sequence No. 14, template peptides from microbicidal domains of PMPs 1 and 2, as illustrated in FIG. 1. These peptides exert rapid (less than 2 hours) and potent (nanomolar concentration) microbicidal activities against a spectrum of pathogens in vitro, many of which are resistant to conventional antibiotics, as is shown in FIGS. 2a and 2b, reflecting in three-dimensional graphs the antimicrobial spectra of RP-1, Sequence No. 3, and RP-13, Sequence No. 14, in vitro (radial diffusion assay). Inocula were $1 \times 10^6$ CFU/ml, and incubation conditions were pH 7.2 (RP-1, Sequence No. 3) or pH 5.5 (RP-13, Sequence No. 14), for 24 hours at 37° C. (Key: EC, *E. coli*; EF, *Ent. faecalis*; PA, *Ps. aeruginosa*; SM, *St. mutans*; SA, *S. aureus* (MRSA); SE, *S. epidermidis* (MRSE); CA, *C. albicans*; CN, *Crypto. neoformans*) Moreover, these templates differ in secondary structure (α-helix vs. β-sheet, respectively) as determined by FTIR spectroscopy and molecular modeling, and have differential pH optima for microbicidal activity (pH 7.2 vs. 5.5, respectively). Thus, the use of peptides derived from these templates will provide complementary opportunities to examine the relationship among peptide structure, microbicidal activity, pathogen specificity, mechanism of action, conditions for activity, and mammalian cell toxicity.

With reference to FIGS. 2A and 2B, designs for novel microbicidal metapeptides should maximize peptide parameters believed to be integral to microbicidal activity: 1) mean hydrophobic moment ($M_H$); 2) charge-to-surface area ratio; 3) charge density; and 4) hydrophobic density. Specific design strategies can include charge substitution, non-polar substitution, aromatic substitution, peptide extension or truncation, and use of D-enantiomers, retromer, retroenantiomer, N-ε-monomethyl-lysine, or other amino acids not normally found in native peptides, or any combination of these approaches.

In charge substitution, charged amino acids can be substituted with alternate amino acids such that the overall charge is essentially conserved. Examples of interchangeable residues where charge conservation substitution can be used to create novel peptides are lysine and arginine, or aspartic acid and glutamic acid.

Peptides can also be designed with substituted non-polar residues to study this effect on peptide microbicidal activity. Leucine and isoleucine are common hydrophobic amino acids in antimicrobial peptides. These residues have a significant impact on hydrophobic density and mean hydrophobic moment ($M_H$) as they relate to peptide microbicidal activity.

Peptides with enhanced microbicidal activity and reduced mammalian cell toxicity can also be generated with aromatic substitutions. Aromatic acids such as tyrosine, phenylalanine, and tryptophan are believed to influence mean hydrophobic moment as well as hydrophobic density.

Peptide extension or truncation can also be used to model peptide designs with strategic modifications. Peptides of reduced chain length generally exhibit features which may be advantageous as potential therapeutic agents as compared with larger proteins: 1) smaller peptides typically have greater distribution via more efficient diffusion; 2) they are generally less immunogenic than larger peptides; and 3) shorter peptides tend to be less susceptible to proteolytic degradation than comparable larger peptides. Selected peptides which exhibit potent microbicidal activity can also be synthesized as N-ε-monomethyl-lysine and/or D-amino acid analogues. This strategy can be useful to increase specificity, reduce toxicity, and extend half-life of these peptides.

Peptides derived from RP-1, Sequence No. 3, and RP-13, Sequence No. 14, or other novel templates will be suitable in mass to model by energy based methods. This approach can be used to identify stable conformers, and thus the most likely to retain structures believed to confer microbicidal function. Phi (φ) and psi (ψ) angles can be assigned systematically; those incompatible with Ramachandran indices for particular amino acids can be rejected to speed the search process. Conformer side chains can be rotated to relieve unstable steric configurations, and promising conformers can be partially minimized using AMBER force-field strategies. Lowest energy conformers can be further analyzed by molecular dynamics to determine stability. The Brookhaven data base can also be searched for peptides homologous to RP-1, Sequence No. 3, and RP-13, Sequence No. 14, which can be used as comparative templates. Side chain contacts can be relieved and minimized by molecular mechanics, and lowest energy conformations analyzed by molecular dynamics. Data from these manipulations can be used to remodel RP-1, Sequence No. 3, RP-13, Sequence No. 14, or other template peptides to further enhance their antimicrobial properties, and reduce their toxicity.

Conformation of peptides can also be significantly influenced by solvation. Promising peptides identified can be solvated in TIP3 water. Solvent effects on molecular dynamic trajectories can be analyzed, and free energy perturbations used to assess solvent energies. Selected solvents can be seeded with counter ions at various concentrations to investigate possible conformational changes in peptides induced by ionic interactions. Furthermore, antimicrobial peptides likely interact with lipid bilayers. At the junction between the aqueous phase and the lipid bilayer, lipid polar head groups create a unique environment; this environment can produce alterations in peptide conformation. Lipid environments (bilayers) simulating bacterial or fungal cytoplasmic membranes (e.g. phosphotidyl glycerol or ergesterol) can be tested for interaction with peptides. Two dimensional arrays of polar head groups will be made and immobilized. A uniform solvation field will be used on either side to simulate the aqueous and hydrocarbon environments. This will permit examination of the effect of charge array on peptide conformation in relationship to lipid interaction. The environment of the lipid bilayer can then be simulated by minimizing the dielectric constant, and removing distance-dependent terms in dielectric function. Analysis of molecular dynamics can also be conducted to examine influence of lipid environments on peptide trajectory.

Comparative molecular field analysis (CoMFA) seeks predictions of biological activity from amino acid sequences. CoMFA can be conducted in two ways. First, all peptides can be equilibrated in a common extended conformation, and their side chains relaxed. A conventional CoMFA can then be constructed. This approach takes advantage of the fact that CoMFA does not appeal to any one mechanism of action, and seeks correlations between changes in structure and changes in biological activity.

Induced folding should be implicit in the CoMFA analysis. In a second method, each peptide can be modeled in the lowest energy conformer, and conformers can be used to construct potential fields to be analyzed by CoMFA.

Promising metapeptide derivatives designed from microbicidal templates RP-1, Sequence No. 3, and RP-13, Sequence No. 14, as above can be synthesized by solid-phase Fmoc (9-fluorenyl-methyloxycarbonyl) chemistry. The method is established, and has been extensively used in production of antimicrobial peptides. Preliminary amino acid analysis can be performed on samples of material to estimate overall coupling efficiency and to confirm peptide composition. Peptides can be cleaved and deprotected, and purified by gel filtration (BioGel P-10) and reverse phase-HPLC (RP-HPLC). This latter instrument can be equipped with a variety of columns including C-4, C-8, and C-18 silica-based reversed phases (Vydac), and synthetic phases such as PRP-300 (Hamilton) used to purify crude peptides on a preparative scale. Following purification, peptides can be quantitated by amino acid analysis utilizing the Pico Tag system. Molecular mass of each peptide can then be confirmed by fast atom bombardment or electrospray mass spectrometry. Fourier-Transform infrared spectroscopy (FTIR) and molecular modeling can then be used to verify the predicted secondary structure of synthetic peptides. In some cases, conformational studies can be performed using analytical ultra-centrifugation using established Stokes radius (radius of gyration) predictions to detect possible peptide-peptide interactions. This approach to peptide production and structural confirmation is highly efficient: a peptide can be synthesized, purified, and verified for sequence and conformation over a ten-day period.

Peptides are tested for antimicrobial potency and spectra against a panel of bacterial and fungal pathogens exhibiting multiple antibiotic-resistance. This panel will include both clinical isolates as well as genetically-defined laboratory strains which exhibit MIC values considered resistant to respective antibiotics. Comparative control organisms to those assembled are summarized in Table 1 below.

TABLE 1

| Organism | Control Strain | Bla | Van | Amg | Amb | Flu |
|---|---|---|---|---|---|---|
| Staphylococcus aureus | ATCC 27217 | R | S | R | N/A | N/A |
| Streptococcus pneumoniae | ATCC 35088 | R | S | S | N/A | N/A |
| Enterococcus faecalis | ATCC 47707 | R | R | R | N/A | N/A |
| Escherichia coli | ATCC 43827 | R | S | R | N/A | N/A |
| Pseudomonas aeruginosa | ATCC 17468 | R | R | R | N/A | N/A |
| Candida albicans | ATCC 36082 | N/A | N/A | N/A | S | S |
| Candida krusei | ATCC 32672 | N/A | N/A | N/A | S | R |
| Candida lusitaniae | ATCC 42720 | N/A | N/A | N/A | R | R |

(Key: R, resistant; S, sensitive; Bla, β-lactams; Van, vancomycin; Amg, aminoglycoside; Amb, amphotericin B; Flu, fluconazole.)

A central goal is to correlate peptide structure with function to identify peptides with potent activity and reduced toxicity. Criteria for success are ten-fold increases in potency as compared with templates RP-1, Sequence No. 3, or RP-13, Sequence No. 14. In this regard, it is advantageous to assess the microbiostatic and the microbicidal activities of peptides, and to correlate these activities with mammalian cell toxicity. For all assays, organisms are cultured to logarithmic-phase per NCCLS guidelines.

We have used the agar radial diffusion assay to determine antimicrobial activities of proteins against microbial pathogens in vitro. One million CFU will be mixed into 10 ml (i.e., $1 \times 10^5$ CFU/ml) of melted 1% agarose (in 10 mM $NaHPO_4$ and cooled to 42° C.) containing minimal nutrient and adjusted to either pH 5.5 or pH 7.2. The agar is solidified in culture dishes, and sample wells are formed. Peptides at various concentrations are dissolved in 10 μl of 0.01% acetic acid buffer (pH 5.5 or 7.2), loaded into individual wells, and incubated at 37° C. for three hours. The plate is then overlayed with 1% agarose containing nutrients and incubated (37° C., for at least 24 hours). Peptides purified by RP-HPLC lacking antimicrobial activity are tested in parallel as controls. Zones of inhibition are measured to quantify antimicrobial activity. This assay will not distinguish between microbicidal and microbiostatic actions, but is highly sensitive to peptides with one or both functions.

Minimum inhibitory (MIC) and microbiocidal concentration (MMC) assays can also be performed, and may include a microvolume assay which is used to quantitatively screen peptides for antimicrobial activities. In this assay, suspensions of bacteria or fungi in appropriate media are placed in 100–200 μl final volumes in microtiter plates. Poly-L-lysine coated or otherwise positively charged plates are used for these assays, since cationic peptides may bind to anionic surfaces. Purified peptides are then serially diluted, descending from 100 μg/ml. Organisms are inoculated into wells to a concentration of $1 \times 10^5$ CFU/ml, and plates incubated (37° C., for at least 24 hours). Well turbidities are then assessed visually and by spectrophotometry to quantify growth inhibition versus wells containing no peptide. MMCs are then determined by quantitative culture of MIC wells exhibiting no visible growth.

Microbicidal kinetics of purified peptides are assessed by resuspending the peptides in 0.01% acetic acid buffer (pH 5.5 or 7.2), and organisms are resuspended to a concentration of $1 \times 10^5$ CFU/ml in 50–250 μl of sterile buffer containing peptide concentrations from 0 to 40 μg/ml. Controls contain buffer alone or non-antimicrobial proteins and organism as above. Mixtures are incubated at 37° C. for up to 48 hours, after which aliquots are quantitatively cultured and incubated for 24 to 48 hours. Killing is expressed as decrease in $logarithm_{10}$ surviving CFU/ml. The limit of sensitivity in microbicidal assays is considered to be a 1 log reduction in viable cells.

Flow cytometry can also be used to examine kinetics and mechanisms of the action of the peptides on bacterial membrane integrity and energetics. Peptides which differ in activity or specificity for their ability to depolarize and/or permeabilize microbial membranes can also be compared by analysis of membrane depolarization, and permeabilization. $DiOC_5$ is a charged lipophilic dye which partitions into the cytoplasm, and is dependent on intact Δψ for intracellular retention. Organisms prepared as above are labeled in darkness for 30 minutes at about 20° C. in PBS containing 0.05 μM $DiOC_5$. Organisms are resuspended to a concentration of $5 \times 10^8$ CFU/ml in K$^+$MEM containing an individual peptide, and incubated at 37° C. For flow cytometry, organisms are washed, sonicated, counted, and resuspended in K$^+$MEM buffer. Reductions in mean $DiOC_5$ fluorescence relative to controls are interpreted to represent loss of $DiOC_5$, indicating membrane depolarization. Positive control cells exposed to valinomycin, as well as control cells not exposed to any peptides, are analyzed for $DiOC_5$ fluorescence in parallel.

Propidium iodide is excluded from cells with normal membrane integrity, but enters cells permealized to molecules ≧2 nm in diameter, and can be stimulated to emit fluorescence at >620 nm. Organisms prepared as above are resuspended to a concentration of 5×10$^8$ CFU/ml in K+MEM containing a selected peptide, and incubated for pre-selected times (ranging from zero up to about 120 minutes) at 37° C. Cells are washed in fresh K+MEM, sonicated, counted, and resuspended in K$^+$MEM buffer containing 20 μM propidium iodide. Control cells exposed to ethanol (positive control for permeabilization) are assessed for propidium iodide uptake in parallel. Increases in mean propidium iodide fluorescence relative to control cells are interpreted to indicate increases in permeability.

Erythrocyte permeabilizing and hemolytic activities of peptides exhibiting potent microbicidal activity are also studied as indicators of potential in vivo toxicity. Four-percent (vol/vol) of washed human erythrocytes (in PBS alone, or in PBS plus 10% heat-inactivated PNHS are incubated with selected peptides ranging in concentration up to 100 times greater than geometric mean MICs. After 24 hours of incubation at 37° C., erythrocyte permeabilization and hemolysis are determined spectrophotometrically. Permeabilization and hemolysis will be compared to buffers alone, and with a triton X-100 control (100% hemolysis).

Endothelial cell injury due to peptides is measured using a standard $^{51}$Cr release assay, described in Filler, S. G., et al., "Candida stimulates endothelial cell eicosanoid production" J Infect Dis. 1991, 164:928–935; Filler, S. G., et al., "Mechanisms by which *Candida albicans* stimulates endothelial cell prostaglandin synthesis" Infect Immun. 1994, 62:1064–1069; Filler, S. G., et al., "Penetration and damage of endothelial cells by *Candida albicans*" Infect Immun. 1995, 63:976–983. Briefly, endothelial cells in 96 well tissue culture plates are incubated with Na$^{51}$CrO$_4$ overnight. The following day, the unincorporated isotope tracer is removed by rinsing, and peptides in 0.01% acetic acid buffer are added to the endothelial cells. Control wells are exposed to buffer alone. After a predetermined incubation period, the medium is aspirated and the amount of $^{51}$Cr released into the medium is measured by scintillation. This approach facilitates toxicity screening of multiple peptides simultaneously, and minimizes the amount of peptide necessary for assessment.

Each antimicrobial and toxicity assay described above is performed independently a minimum of two times, and means ±standard error is calculated for each peptide under varying exposure conditions (concentration or pH) as compared with control samples. Statistical analyses of microbicidal data are performed using Student t test or Kruskall-Wallis rank sum analysis for non-parametric data, and corrected for multiple comparisons as appropriate.

The antimicrobial peptides and derived metapeptides for potentiating antimicrobial agents active against organisms such as bacteria and fungi can thus comprise peptides having amino acid sequences selected from the group consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX. B can be, for example, at least one positively charged amino acid, X can be, for example, at least one non-polar, hydrophobic amino acid, and Z can be, for example, at least one aromatic amino acid. For example, B can be selected from the group of amino acids consisting of lysine, arginine, histidine, and combinations thereof; X can be selected from the group of amino acids consisting of leucine, isoleucine, alanine, valine, and combinations thereof; and Z can be selected from the group of amino acids consisting of phenylalanine, tryptophan, tyrosine and combinations thereof.

The first peptide template XZBZBXBXB corresponds to the peptide template RP-1, Sequence No. 3; and the second peptide template XBBXX corresponds to the peptide template RP-13, Sequence No. 14.

Figure 3:
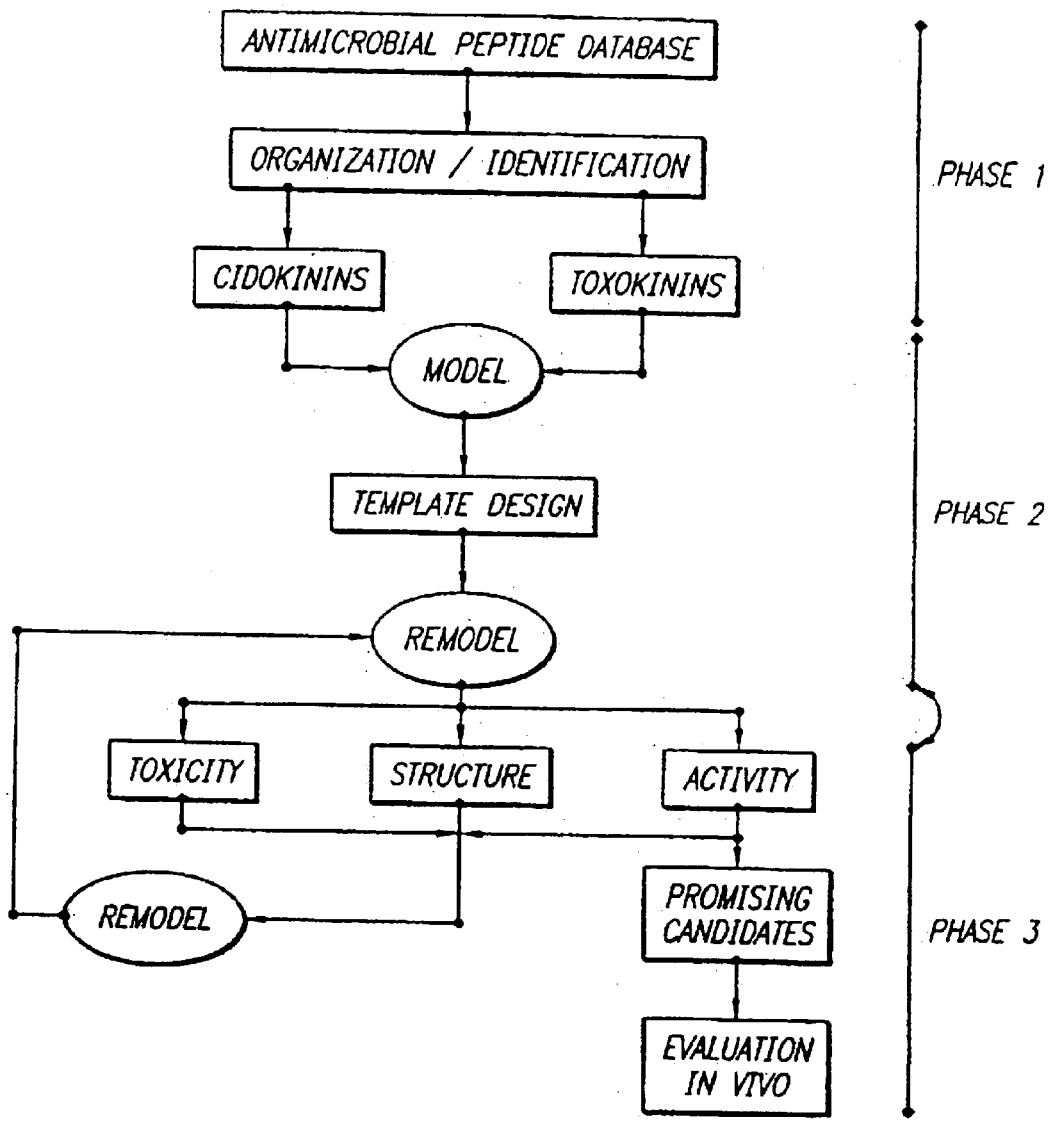
FIG. 3 is a flow chart illustrating the method for developing the novel antimicrobial peptides according to the principles of the invention.

The method for developing the novel antimicrobial peptides according to the principles of the invention is summarized in the flow chart shown in FIG. 3. Initially, the antimicrobial peptide database is inspected visually, and the literature is reviewed, utilizing comparative sequence techniques, in order to identify likely antimicrobial peptide domains. Cidokinins (peptide domains associated with antimicrobial activity) and toxokinins (peptide domains asociated with mammalian cell toxicity) are organized and domains and structural motifs are identified, and modeled to maximize the cidokinins and minimize the toxokinins. From this modeling, template designs such as RP13 are devised, and in turn are used for remodeling, by testing for toxicity, structure and antimicrobial activity, to identify promising candidates for further evaluation in vivo.

It will be apparent from the foregoing that while particular forms of the invention have been illustrated and described, various modifications can be made without departing from the spirit and scope of the invention.

What is claimed is:

1. An antimicrobial peptide comprising an amino acid sequence selected from the group consisting of RP-1 (SEQ ID NO: 3), RP-8 (SEQ ID NO: 10), RP-11 (SEQ ID NO: 13) and RP-13 (SEQ ID NO: 14).

* * * * *

SEQUENCE LISTING

<160> NUMBER OF SEQ ID NOS: 38

<210> SEQ ID NO 1
<211> LENGTH: 74
<212> TYPE: PRT
<213> ORGANISM: Oryctolagus cuniculus

<400> SEQUENCE: 1

Ser Asp Asp Pro Lys Glu Ser Glu Gly Asp Leu His Cys Val Cys
1               5                   10                  15

Lys Thr Thr Ser Leu Val Arg Pro Arg His Ile Thr Asn Leu Glu Leu
            20                  25                  30

Ile Lys Ala Gly Gly His Cys Pro Thr Ala Asn Leu Ile Ala Thr Lys

```
                35                  40                  45
Lys Asn Gly Arg Lys Leu Cys Leu Asp Leu Gln Ala Ala Leu Tyr Lys
        50                  55                  60
Lys Lys Ile Ile Lys Lys Leu Leu Glu Ser
65                  70

<210> SEQ ID NO 2
<211> LENGTH: 74
<212> TYPE: PRT
<213> ORGANISM: Oryctolagus cuniculus

<400> SEQUENCE: 2

Ser Asp Asp Pro Lys Glu Ser Glu Gly Asp Leu His Cys Val Cys Val
1               5                   10                  15

Lys Thr Thr Ser Leu Val Arg Pro Gly His Ile Thr Asn Leu Glu Leu
            20                  25                  30

Ile Lys Ala Gly Gly His Cys Pro Thr Ala Asn Leu Ile Ala Thr Lys
        35                  40                  45

Lys Asn Gly Arg Lys Leu Cys Leu Asp Leu Gln Ala Ala Leu Tyr Lys
        50                  55                  60

Lys Lys Ile Ile Lys Lys Leu Leu Glu Ser
65                  70

<210> SEQ ID NO 3
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 3

Ala Leu Tyr Lys Lys Phe Lys Lys Leu Leu Lys Ser Leu Lys Arg
1               5                   10                  15

Leu Gly

<210> SEQ ID NO 4
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 4

Ala Arg Tyr Lys Lys Phe Lys Lys Lys Leu Leu Lys Ser
1               5                       10

<210> SEQ ID NO 5
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 5

Lys Leu Tyr Arg Lys Phe Lys Asn Lys Leu Leu Lys Leu Lys
1               5                   10
```

```
<210> SEQ ID NO 6
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 6

Ala Arg Tyr Arg Lys Phe Lys Asn Lys Ile Leu Lys Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 7

Ala Arg Tyr Arg Lys Phe Arg Asn Lys Ile Leu Arg Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 8

Lys Leu Tyr Lys Lys Trp Lys Lys Lys Leu Leu Lys Leu Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 9

Ala Leu Tyr Lys Lys Trp Lys Asn Lys Leu Leu Lys Ser
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 10

Lys Leu Tyr Lys Lys Trp Lys Asn Lys Leu Lys Arg Ser Leu Lys Arg
1               5                   10                  15

Leu Gly

<210> SEQ ID NO 11
<211> LENGTH: 13
```

```
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 11

Ala Leu Tyr Lys Lys Leu Phe Lys Lys Leu Leu Lys Arg
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 12

Gly Leu Tyr Lys Arg Leu Phe Lys Lys Leu Leu Lys Ser
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 13

Ala Leu Tyr Lys Arg Leu Phe Lys Lys Leu Lys Lys Phe
 1               5                  10

<210> SEQ ID NO 14
<211> LENGTH: 17
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 14

Ala Thr Lys Lys Asn Gly Arg Lys Leu Cys Leu Asp Leu Gln Ala Ala
 1               5                  10                  15

Leu

<210> SEQ ID NO 15
<211> LENGTH: 8
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 15

Arg Phe Glu Lys Ser Lys Ile Lys
 1               5

<210> SEQ ID NO 16
<211> LENGTH: 20
<212> TYPE: PRT
<213> ORGANISM: Artificial Sequence
```

```
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 16

Ser Ala Ile His Pro Ser Ser Ile Leu Lys Leu Glu Val Ile Cys Ile
 1               5                  10                  15

Gly Val Leu Gln
         20

<210> SEQ ID NO 17
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 17

Tyr Ala Glu Arg Leu Cys Thr Cys Ser Ile Lys Ala Glu Val
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 18

Lys Phe Lys His Tyr Phe Phe Trp Lys Tyr Lys
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 19

Lys Gly Tyr Phe Tyr Phe Leu Phe Lys Phe Lys
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 20

Lys Trp Lys Trp Trp Trp Trp Lys Trp Lys
 1               5                  10

<210> SEQ ID NO 21
<211> LENGTH: 13
<212> TYPE: PRT
<213> ORGANISM: Artificial Sequence
<220> FEATURE:
```

```
-continued

<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 21

Pro Arg Ile Lys Lys Ile Val Gln Lys Lys Leu Ala Gly
1               5                   10

<210> SEQ ID NO 22
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 22

Lys Trp Val Arg Glu Tyr Ile Asn Ser Leu Glu Met Ser Lys Lys Gly
1               5                   10                  15

Leu Ala Gly

<210> SEQ ID NO 23
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 23

Glu Trp Val Gln Lys Tyr Val Ser Asp Leu Glu Leu Ser Ala Trp Lys
1               5                   10                  15

Lys Ile Leu Lys
            20

<210> SEQ ID NO 24
<211> LENGTH: 12
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 24

Ser Trp Val Gln Glu Tyr Val Tyr Asp Leu Glu Leu
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 25

Ala Asp Ser Gly Glu Gly Asp Phe Leu Ala Glu Gly Gly Gly Val Arg
1               5                   10                  15

<210> SEQ ID NO 26
<211> LENGTH: 20
<212> TYPE: PRT
<213> ORGANISM: Artificial Sequence
```

```
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 26

Ala Asp Ser Gly Glu Gly Asp Phe Leu Ala Glu Gly Gly Val Arg
1               5                   10                  15

Lys Leu Ile Lys
            20

<210> SEQ ID NO 27
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 27

Glu Gly Val Asn Asp Asn Glu Glu Gly Phe Phe Ser Ala
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 28

Lys Phe Asp Lys Ser Lys Leu Lys Lys Thr Glu Thr Gln Glu Lys Asn
1               5                   10                  15

Pro Leu

<210> SEQ ID NO 29
<211> LENGTH: 15
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 29

Ala Asn Leu Ile Ala Thr Lys Lys Asn Gly Arg Lys Leu Cys Leu
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(0)
<223> OTHER INFORMATION: Xaa =Alanine, Lysine or Glycine
<221> NAME/KEY: VARIANT
<222> LOCATION: (2)...(0)
<223> OTHER INFORMATION: Xaa = Leucine or Arginine
<221> NAME/KEY: VARIANT
<222> LOCATION: (4)...(5)
<223> OTHER INFORMATION: Xaa = Lysine, Arginine or Histidine
<221> NAME/KEY: VARIANT
<222> LOCATION: (6)...(0)
<223> OTHER INFORMATION: Xaa =Phenylalanine, Tryptophan and Tyrosine.
```

```
<221> NAME/KEY: VARIANT
<222> LOCATION: (7)...(0)
<223> OTHER INFORMATION: Xaa = Lysine or Arginine
<221> NAME/KEY: VARIANT
<222> LOCATION: (8)...(0)
<223> OTHER INFORMATION: Xaa = Lysine or Asparigine
<221> NAME/KEY: VARIANT
<222> LOCATION: (10)...(0)
<223> OTHER INFORMATION: Xaa = Leucine or Isoleucine
<221> NAME/KEY: VARIANT
<222> LOCATION: (11)...(0)
<223> OTHER INFORMATION: Xaa = Leucine or Lysine
<221> NAME/KEY: VARIANT
<222> LOCATION: (12)...(0)
<223> OTHER INFORMATION: Xaa = Lysine or Arginine

<400> SEQUENCE: 30

Xaa Xaa Tyr Xaa Xaa Xaa Xaa Xaa Lys Xaa Xaa Xaa
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(5)
<223> OTHER INFORMATION: Xaa = Any amino acid
<221> NAME/KEY: VARIANT
<222> LOCATION: (6)...(0)
<223> OTHER INFORMATION: Xaa = Phenylalanine, Tryptophan or Tyrosine
<221> NAME/KEY: VARIANT
<222> LOCATION: (7)...(0)
<223> OTHER INFORMATION: Xaa = Lysine or Arginine
<221> NAME/KEY: VARIANT
<222> LOCATION: (8)...(12)
<223> OTHER INFORMATION: Xaa = Any amino acid

<400> SEQUENCE: 31

Xaa Xaa Xaa Xaa Xaa Xaa Xaa Xaa Xaa Xaa Xaa Xaa
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(5)
<223> OTHER INFORMATION: Xaa = Any amino acid
<221> NAME/KEY: VARIANT
<222> LOCATION: (6)...(0)
<223> OTHER INFORMATION: Xaa = Phenylalanine or Tryptophan
<221> NAME/KEY: VARIANT
<222> LOCATION: (7)...(0)
<223> OTHER INFORMATION: Xaa = Lysine, Arginine or Leucine
<221> NAME/KEY: VARIANT
<222> LOCATION: (8)...(12)
<223> OTHER INFORMATION: Xaa = Any amino acid

<400> SEQUENCE: 32

Xaa Xaa Xaa Xaa Xaa Xaa Xaa Xaa Xaa Xaa Xaa Xaa
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
```

```
<222> LOCATION: (1)...(5)
<223> OTHER INFORMATION: Xaa = Any amino acid
<221> NAME/KEY: VARIANT
<222> LOCATION: (6)...(0)
<223> OTHER INFORMATION: Xaa = Lysine, Arginine or Leucine
<221> NAME/KEY: VARIANT
<222> LOCATION: (7)...(0)
<223> OTHER INFORMATION: Xaa = Phenylalanine or Tryptophan
<221> NAME/KEY: VARIANT
<222> LOCATION: (8)...(12)
<223> OTHER INFORMATION: Xaa = Any amino acid

<400> SEQUENCE: 33

Xaa Xaa Xaa Xaa Xaa Xaa Xaa Xaa Xaa Xaa Xaa Xaa
  1               5                  10

<210> SEQ ID NO 34
<211> LENGTH: 7
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(5)
<223> OTHER INFORMATION: Xaa = Any amino acid
<221> NAME/KEY: VARIANT
<222> LOCATION: (6)...(0)
<223> OTHER INFORMATION: Xaa = Phenylalanine, Tryptophan or Tyrosine
<221> NAME/KEY: VARIANT
<222> LOCATION: (7)...(0)
<223> OTHER INFORMATION: Xaa = Lysine or Arginine

<400> SEQUENCE: 34

Xaa Xaa Xaa Xaa Xaa Xaa Xaa
  1               5

<210> SEQ ID NO 35
<211> LENGTH: 13
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(5)
<223> OTHER INFORMATION: Xaa = Any amino acid
<221> NAME/KEY: VARIANT
<222> LOCATION: (6)...(0)
<223> OTHER INFORMATION: Xaa = Phenylalanine or Tyrptophan
<221> NAME/KEY: VARIANT
<222> LOCATION: (7)...(0)
<223> OTHER INFORMATION: Xaa = Lysine, Arginine or Lysine
<221> NAME/KEY: VARIANT
<222> LOCATION: (8)...(12)
<223> OTHER INFORMATION: Xaa = Any amino acid
<221> NAME/KEY: VARIANT
<222> LOCATION: (13)...(0)
<223> OTHER INFORMATION: Xaa = Serine, Leucine, Arginine or
      Phenylalanine

<400> SEQUENCE: 35

Xaa Xaa Xaa Xaa Xaa Xaa Xaa Xaa Xaa Xaa Xaa Xaa Xaa
  1               5                  10

<210> SEQ ID NO 36
<211> LENGTH: 13
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(5)
<223> OTHER INFORMATION: Xaa = Any amino acid
<221> NAME/KEY: VARIANT
```

```
<222> LOCATION: (6)...(0)
<223> OTHER INFORMATION: Xaa = Lysine, Arginine or Leucine
<221> NAME/KEY: VARIANT
<222> LOCATION: (7)...(0)
<223> OTHER INFORMATION: Xaa = Phenylalanine or Tryptophan
<221> NAME/KEY: VARIANT
<222> LOCATION: (8)...(12)
<223> OTHER INFORMATION: Xaa = Any amino acid
<221> NAME/KEY: VARIANT
<222> LOCATION: (13)...(0)
<223> OTHER INFORMATION: Xaa = Serine, Leucine, Arginine or
      Phenylalanine

<400> SEQUENCE: 36

Xaa Xaa Xaa Xaa Xaa Xaa Xaa Xaa Xaa Xaa Xaa Xaa Xaa
 1               5                   10

<210> SEQ ID NO 37
<211> LENGTH: 17
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (1)...(2)
<223> OTHER INFORMATION: Xaa = Leucine, Isoleucine, Alanine, Valine,
      Serine, Glycine or Threonine
<221> NAME/KEY: VARIANT
<222> LOCATION: (3)...(4)
<223> OTHER INFORMATION: Xaa = Lysine Arginine, Histidine, Glutamine or
      Proline
<221> NAME/KEY: VARIANT
<222> LOCATION: (5)...(0)
<223> OTHER INFORMATION: Xaa = Asparagine, Cystine, Aspartic Acid,
      Glutamic Acid or Methionine
<221> NAME/KEY: VARIANT
<222> LOCATION: (6)...(0)
<223> OTHER INFORMATION: Xaa = Leucine, Isoleucine, Alanine, Valine,
      Serine, Glycine or Threonine
<221> NAME/KEY: VARIANT
<222> LOCATION: (7)...(0)
<223> OTHER INFORMATION: Xaa = Lysine, Arginine, Histidine, Glutamine,
      Proline, Glutamic Acid or Glycine
<221> NAME/KEY: VARIANT
<222> LOCATION: (8)...(0)
<223> OTHER INFORMATION: Xaa = Lysine, Arginine, Histidine, Glutamine,
      Proline and Glutamic Acid
<221> NAME/KEY: VARIANT
<222> LOCATION: (9)...(0)
<223> OTHER INFORMATION: Xaa = Leucine, Isoleucine, Alanine, Valine,
      Serine, Glycine or Threonine
<221> NAME/KEY: VARIANT
<222> LOCATION: (10)...(0)
<223> OTHER INFORMATION: Xaa = Asparagine, Cystine, Aspartic Acid,
      Glutamine Acid or Methionine
<221> NAME/KEY: VARIANT
<222> LOCATION: (11)...(0)
<223> OTHER INFORMATION: Xaa = Leucine, Isoleucine, Alanine, Valine,
      Serine, Glycine or Threonine
<221> NAME/KEY: VARIANT
<222> LOCATION: (12)...(0)
<223> OTHER INFORMATION: Xaa = Asparagine, Cystine, Aspartic Acid,
      Glutamine Acid or Methionine
<221> NAME/KEY: VARIANT
<222> LOCATION: (13)...(0)
<223> OTHER INFORMATION: Xaa = Leucine, Isoleucine, Alanine, Valine,
      Serine, Glycine or Threonine
<221> NAME/KEY: VARIANT
<222> LOCATION: (14)...(0)
<223> OTHER INFORMATION: Xaa = Lysine, Arginine, Histidine, Glutamine or
      Proline
<221> NAME/KEY: VARIANT
<222> LOCATION: (15)...(17)
<223> OTHER INFORMATION: Xaa = Leucine, Isoleucine, Alanine, Valine,
      Serine, Glycine or Threonine

<400> SEQUENCE: 37
```

Xaa Xaa Xaa Xaa Xaa Xaa Xaa Xaa Xaa Xaa Xaa Xaa Xaa Xaa Xaa
1               5                   10                  15

Xaa

<210> SEQ ID NO 38
<211> LENGTH: 14
<212> TYPE: PRT
<213> ORGANISM: Artificial Sequence
<220> FEATURE:
<223> OTHER INFORMATION: Antimicrobiocidal peptide template core.
<221> NAME/KEY: VARIANT
<222> LOCATION: (7)...(0)
<223> OTHER INFORMATION: Xaa = Valine or Threonine

<400> SEQUENCE: 38

Tyr Ala Glu Arg Leu Cys Xaa Cys Ser Ile Lys Ala Glu Val
1               5                   10